US 9,903,842 B2

United States Patent
Bannouf et al.

(10) Patent No.: US 9,903,842 B2
(45) Date of Patent: Feb. 27, 2018

(54) METHOD FOR PROCESSING SIGNALS ACQUIRED BY ULTRASONIC PROBING, CORRESPONDING PROGRAM AND ULTRASONIC PROBING DEVICE

(71) Applicant: COMMISSARIAT A L'ENERGIE ATOMIQUE ET AUX ENE ALT, Paris (FR)

(72) Inventors: Souad Bannouf, Epinay sur Seine (FR); Olivier Casula, Longpont-sur-Orge (FR); Claire Prada Julia, Paris (FR); Sebastien Robert, Le Kremlin-Bicetre (FR)

(73) Assignee: Commissariat a l'energie atomique et aux energies alternatives, Paris (FR)

(*) Notice: Subject to any disclaimer, the term of this patent is extended or adjusted under 35 U.S.C. 154(b) by 437 days.

(21) Appl. No.: 14/414,263

(22) PCT Filed: Jul. 12, 2013

(86) PCT No.: PCT/FR2013/051677
§ 371 (c)(1),
(2) Date: Jan. 12, 2015

(87) PCT Pub. No.: WO2014/009671
PCT Pub. Date: Jan. 16, 2014

(65) Prior Publication Data
US 2015/0212051 A1   Jul. 30, 2015

(30) Foreign Application Priority Data

Jul. 12, 2012   (FR) .................................. 12 56718

(51) Int. Cl.
| | | |
|---|---|---|
| *G01N 29/44* | (2006.01) | |
| *G01S 15/89* | (2006.01) | |
| *G01N 29/06* | (2006.01) | |
| *G01N 29/26* | (2006.01) | |
| *G01N 29/46* | (2006.01) | |
| *G01N 29/24* | (2006.01) | |
| *G01S 7/52* | (2006.01) | |
| *G01S 15/00* | (2006.01) | |

(Continued)

(52) U.S. Cl.
CPC .......... *G01N 29/44* (2013.01); *G01N 29/069* (2013.01); *G01N 29/24* (2013.01); *G01N 29/262* (2013.01);
(Continued)

(58) Field of Classification Search
CPC .......... G01N 2291/106; G01N 29/069; G01N 29/0654; G01N 29/44; G01S 15/8927;
(Continued)

(56) References Cited

U.S. PATENT DOCUMENTS

2005/0154306 A1   7/2005   Burgher et al.
2011/0125014 A1   5/2011   Derode et al.

OTHER PUBLICATIONS

International Search Report dated Oct. 28, 2013, in PCT/FR13/051677 filed Jul. 12, 2013.
(Continued)

*Primary Examiner* — Huan Tran
(74) *Attorney, Agent, or Firm* — Oblon, McClelland, Maier & Neustadt, L.L.P.

(57) ABSTRACT

A method for processing ultrasonic signals includes: controlling a plurality of emission transducers for L successive emissions of ultrasonic waves; controlling N reception transducers to simultaneously receive and for a predetermined time, for each successive emission, N measurement signals; obtaining an array of ultrasonic time signals of size L×N, each coefficient $K_{i,j}(t)$ of this array representing the measurement signal received by the j-th reception transducer due to the i-th emission; and denoising the time signal array by removing some of the singular values and associated singular vectors obtained from a singular value decomposition of a frequency signal array obtained by transforming this time signal array, and by reconstructing a denoised time signal array based on unremoved singular values and singular vectors.

11 Claims, 3 Drawing Sheets

Figure 1:
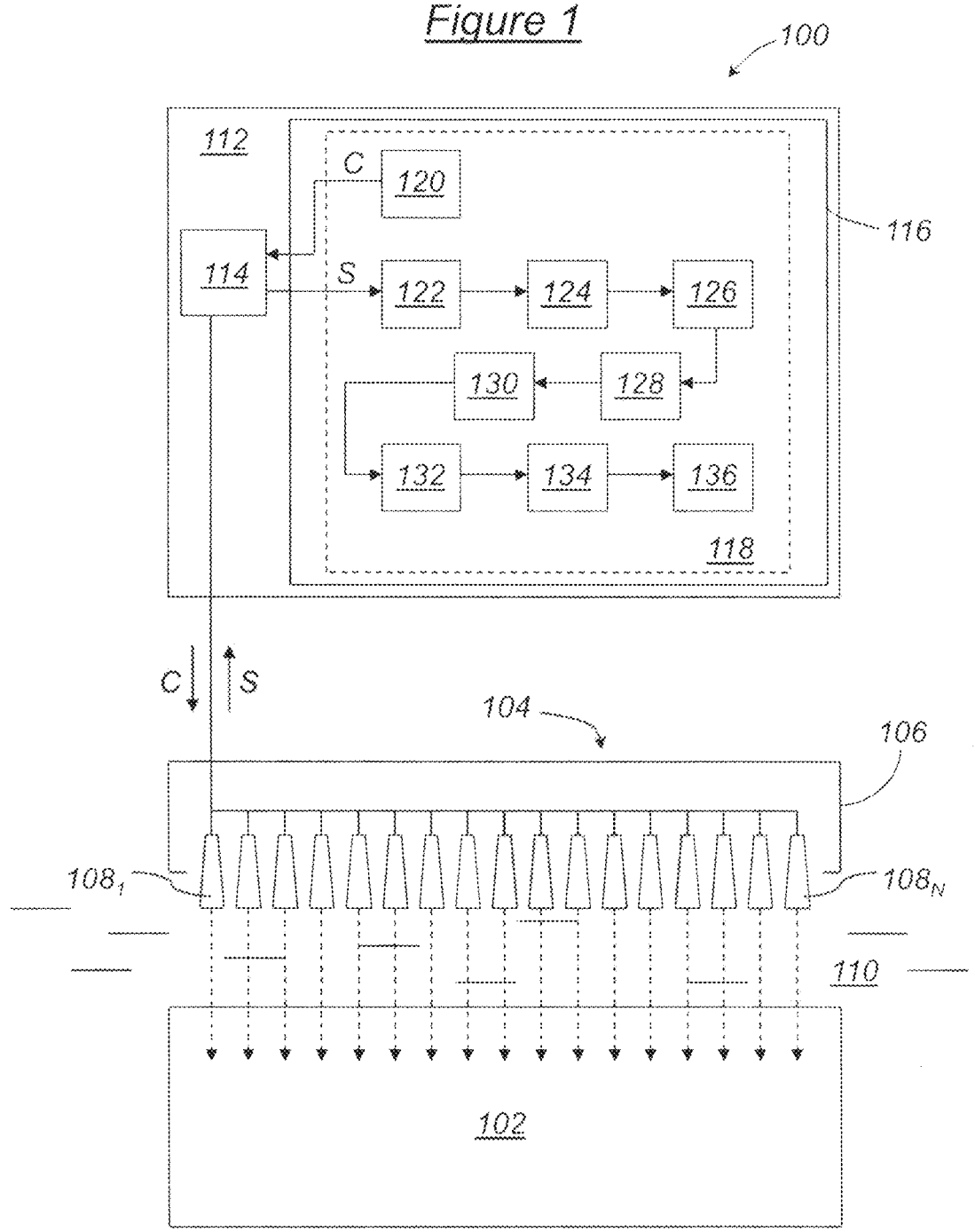

(52) U.S. Cl.
CPC ......... *G01N 29/4472* (2013.01); *G01N 29/46* (2013.01); *G01S 7/52077* (2013.01); *G01S 15/8927* (2013.01); *G01S 15/8977* (2013.01); *G01N 2291/0289* (2013.01); *G01N 2291/106* (2013.01); *G01S 7/52046* (2013.01); *G01S 15/006* (2013.01)

(58) Field of Classification Search
CPC ............ G01S 15/8977; G01S 15/8997; G01S 7/52085; G01S 15/8915
See application file for complete search history.

(56) References Cited

OTHER PUBLICATIONS

French Preliminary Search Report dated Mar. 26, 2013, in French Application No. 12 56718 filed Jul. 12, 2012.

Minonzio, et al., "Measurement of guided mode wave vectors by analysis of the transfer matrix obtained with multi-emitters and multi-receivers in contact", Journal of Physics: Conference Series, vol. 269, XP055057744, Jan. 2011, 8 pages.

Minonzio, et al., "Measurement of guided mode phase velocities using multi-emitters and multi-receivers arrays in contact and transmission matrix analysis", Ultrasonic Symposium (IUS), 2009 IEEE International Ultrasonics Symposium Proceedings, XP031818155, Sep. 20, 2009, pp. 578-581.

Fidahoussen, et al., "Imaging of Defects in Several Complex Configurations by Simulation-Helped Processing of Ultrasonic Array Data", Review of Quantitative Nondestructive Evaluation, vol. 29, 2009, 8 pages.

Prada, et al., "Eigenmodes of the time reversal operator: A solution to selective focusing in multiple-target media", Wave Motion 20, Elsevier, 1994, pp. 151-163.

Karaman, et al., "Synthetic Aperture Imaging for Small Scale Systems", IEEE Transactions on Ultrasonics, Ferroelectrics, and Frequency Control, vol. 42, No. 3, May 1995, pp. 429-442.

Holmes, et al., "Post-processing of the full matrix of ultrasonic transmit-receive array data for non-destructive evaluation", NDT&E International 38, Elsevier, 2005, pp. 701-711.

METHOD FOR PROCESSING SIGNALS ACQUIRED BY ULTRASONIC PROBING, CORRESPONDING PROGRAM AND ULTRASONIC PROBING DEVICE

The present invention relates to a method for processing signals acquired by ultrasonic probing, particularly for performing ultrasonic imaging. It also relates to a corresponding computer program and ultrasonic probing device.

The invention is particularly applicable to the field of ultrasonic non-destructive testing, wherein the acquisition of ultrasonic signals makes it possible to view and detect defects in structures, but it may also be applied to any type of ultrasonic echographic imaging, particularly in the medical field for inspecting areas of interest in the human or animal body.

It relates more particularly to a processing method acquiring ultrasonic signals as follows:
- controlling a plurality of emission transducers for L successive emissions of ultrasound waves to an area of interest,
- controlling N reception transducers so as to simultaneously receive and for a predetermined time, for each successive emission, N measurement signals, particularly measuring noisy echoes due to reflections of the emission in question in the area of interest,
- obtaining an array of ultrasonic time signals of the size L×N, each coefficient $K_{i,j}(t)$ of this array representing the measurement signal received by the j-th reception transducer due to the i-th emission.

Such an acquisition is generally performed using a multielement sensor probing device, wherein each transducer is both transmitter and receiver, where switching between these two modes may be controlled electronically. The sensor may be placed in contact with the object to be probed or at a distance, but in the latter case it should be submerged to ensure the transmission of the ultrasonic waves in the object to be probed. This sensor may be linear (1D) or array-based (2D), with rigid or flexible elements.

The array of time signals obtained using this type of acquisition may then be the subject of processing, particularly for furnishing an image of the area of interest inspected or for retrieving significant structural defect parameters in the area of interest inspected. In view of the computing capability of the processors, this processing may be embedded in the monitoring instruments for real-time processing.

In practice, the ultrasonic acquisition defined above, generally referred to as FMC ("Full Matrix Capture"), consists of emitting an ultrasonic wave by exciting the first emission transducer and receiving the echoes of this emission with the set of N reception transducers, then electronically switching in the set of emission transducers to successively excite these emission transducers. The emission and reception transducers may be located on two separate sensors, but when the same transducers carry out the emission and reception functions, an array K(t) of ultrasonic time signals of the size N×N is obtained.

In the article by C. Holmes et al, entitled "Post-processing of the full matrix of ultrasonic transmit-receive array data for non-destructive evaluation", published in NDT&E International 38 (available online on Jun. 15, 2005), pages 701-711, the coefficients of the array K(t) are used to perform a "total focusing" type synthetic aperture focusing making it possible to obtain a high-resolution image of the area of interest.

More specifically, this synthetic focusing consists of computing for each point of the area of interest the time of flight $T_{i,j}$ corresponding to the travel time between each emission transducer (index i) and each reception transducer (index j) via the point in question (L×N times of flight for each point). Synthetic focusing is performed by summing, for each point of the area of interest, the amplitudes retrieved from the signals $K_{i,j}(t)$ at the times $t=T_{i,j}$. The amplitude A at a point P of the image may thus be expressed as follows:

$$A(P) = \sum_{i=1}^{L} \sum_{j=1}^{N} K_{i,j}[T_{i,j}].$$

Reconstruction using total focusing may be performed according to various known ultrasonic inspection modes: direct mode where the associated times of flight are described above, and other more complex modes where the times of flight include multiple reflections on the boundaries of the structure along with mode conversions. For a detailed explanation of these other more complex modes, reference may particularly be made to the article by A. Fidahoussen et al, entitled "Imaging of defects in several complex configurations by simulation-helped processing of ultrasonic array data", published in Review of Quantitative Nondestructive Evaluation, vol. 29 (2009), pages 847-854.

However, applied to the imaging of noisy parts, reconstruction using total focusing may furnish images of lower quality compared to conventional echographic methods. Indeed, in the latter, all the transducers emit simultaneously by applying a predefined delay sequence so as to focus at a given point. However, according to the FMC acquisition method generally implemented to subsequently conduct reconstruction by means of synthetic aperture focusing, each emission is performed by a single transducer which limits the energy transmitted and the penetration depth of the waves in the inspected part. This is finally conveyed by a degradation of the Signal-To-Noise Ratio (SNR) as the amplitudes of the echo signals may be weaker than the electronic noise. This SNR degradation increases if the object has a high level of structural noise, making the detection and characterization of any defects difficult.

One partial solution to this SNR degradation problem is provided in the article by M. Karaman et al, entitled "Synthetic aperture imaging for small scale systems", published in IEEE Transactions on Ultrasonics, Ferroelectrics, and Frequency Control, vol. 42, No. 3 (May 1995), pages 429-442.

It consists of using, for each emission, no longer one transducer but M adjacent transducers. A delay sequence is applied to the M emission transducers activated so that they transmit a spherical ultrasonic wave in the medium, similar to that which would be emitted by a virtual source situated at a certain distance from the sensor. The ultrasonic wave thus emitted by the virtual source is more intense since the energy thereof is proportional to the square root of the number of transducers forming this source. The SNR is enhanced accordingly, on the assumption that the noise generated is essentially uncorrelated electronic noise.

However, in the case of inspected parts having a high level of structural noise, the enhancement of the quality of the images finally obtained by synthetic total focusing is more limited, the increase in the SNR is lower and the impact on detection is not as positive as may have been hoped. This solution compensates in part for the problem mentioned above but does not eliminate it. Moreover, emitting by means of virtual sources does not help do away with the problem which may be posed by reconstruction artifacts essentially due to parasitic echoes such as geometric echoes or complex echoes including multiple reflections on the boundaries of the object and the mode conversions. Finally, it is noted that for a sensor having N emission/reception transducers, the array K(t) of ultrasonic time signals obtained has the reduced size L×N, where $1 \leq L \leq 5$. N−M+1, M being the number of transducers activated simultaneously to form the virtual source ($1 \leq M \leq N$).

In the article by C. Prada et al, entitled "Eigenmodes of the time reversal operator: a solution to selective focusing in multiple-target media", published in Wave Motion 20 (1994), pages 151-163, the array K(t) is used to perform a decomposition of the time reversal operator defined as being the conjugate product (T indicating the complex conjugate) $K(\omega) \cdot K^T(\omega)$, where $K(\omega)$ corresponds to the Fourier transform of the array K(t). The principle described in this article is that of determining the invariants of this time reversal operator. For this purpose, a singular value decomposition of the frequency signal array $K(\omega)$ obtained using the Fourier transform of the time signal array K(t) is performed following the FMC acquisition. It has indeed been observed that, as a general rule, in the distribution of the singular values obtained, the number of high singular values (i.e. having significant amplitudes) is equal to the number of defects in the part inspected, provided that the defects are sufficiently small and at a distance from each other. Each singular vector thus furnishes the response from a defect (i.e. the Green function thereof) that can be used to focus thereon without needing precise information on the geometric and acoustic properties of the object. This is referred to as the autofocusing principle. The order of the singular vectors is dependent on the more or less scattering nature of the defect. In this way, the first singular vector corresponds to the greatest scatterer, for example the defect closest to the sensor, and so on.

However, this time reversal operator decomposition method is essentially a detection method by retrieving significant parameters demonstrating the limitations thereof in the presence of a high level of structural noise, or when the defects are close to a boundary of the inspected object, for example in the case of a defect close to a part base. Indeed, in these specific cases, no actual separation of a singular value in relation to the others is observed. It is thus in fact difficult to match a singular value to a possible defect. Detection is thus more difficult. Furthermore, unlike the synthetic aperture focusing methods mentioned above, this method does not furnish an image, but merely an indication of the presence of a defect or not. The location and characterization of a defect requires the addition of an imaging algorithm.

It may thus be sought to provide a method for processing ultrasonic signals suitable for doing away with at least some of the problems and constraints mentioned above.

It is therefore proposed a method for processing ultrasonic signals acquired by ultrasonic probing comprising the following steps:
controlling a plurality of emission transducers for L successive emissions of ultrasound waves to an area of interest,
controlling N reception transducers so as to simultaneously receive and for a predetermined time, for each successive emission, N measurement signals, particularly measuring noisy echoes due to reflections of the emission in question in the area of interest,
obtaining an array of ultrasonic time signals of the size L×N, each coefficient Ki,j of this array representing the measurement signal received by the j-th reception transducer due to the i-th emission,
performing a singular value decomposition of a frequency signal array obtained by transforming this time signal array, comprising a step for denoising the ultrasonic time signal array by:
removing some of the singular values and associated singular vectors obtained from said singular value decomposition, and
reconstructing a denoised time signal array from the unremoved singular values and singular vectors.

In this way, the singular value decomposition of the frequency signal array obtained by the transform of the acquired time signal array is used astutely to denoise the latter, since it has been observed that some of these singular values are in fact directly correlated with structural noises from the probed part and/or parasitic echoes (interface echoes) from ultrasonic acquisition by means of a multielement sensor. By thus reconstructing a denoised time signal array, it is then possible to continue conventional processing of the latter, for example to obtain a superior ultrasonic image of the probed area of interest, on the basis of higher quality data.

Optionally, the denoising step is performed by:
transform of the time signal array into a frequency signal array,
singular value decomposition of the frequency signal array,
removing some of the singular values and associated singular vectors according to a predetermined criterion for distinguishing between singular values associated with defects and singular values associated with noise,
reconstructing a denoised frequency signal array on the basis of unremoved singular values and singular vectors,
inverse transform of this denoised frequency signal array into a denoised time signal array.

Also optionally, the predetermined criterion for distinguishing between singular values associated with defects and singular values associated with noise is a criterion relating to successive amplitude differences between singular values in a decreasing series of amplitudes of the singular values determined on the basis of the frequency signal array, for example a curvature change or slope change criterion in this decreasing series of singular value amplitudes.

Also optionally, the transform and inverse transform are discrete Fourier transforms.

Also optionally, a method for processing ultrasonic signals according to the invention may comprise, before the denoising step, a step for filtering the time signal array by deleting any data situated at times of flight excluded from the area of interest.

Also optionally, a method for processing ultrasonic signals according to the invention may comprise a step for reorganizing frequency components of the singular values and singular vectors of the frequency signal array on the basis of an optimization of correlations between frequency occurrences of the singular vectors so as to optimize a correspondence between singular values and defects in the area of interest and thus optimize noise filtering.

Also optionally, at each successive emission, M adjacent emission transducers are activated and a delay sequence is applied to these M emission transducers so as to emit a spherical wave from a virtual source situated at a predetermined distance from said plurality of emission transducers.

Also optionally, each reception is performed by L' virtual reception transducers, each virtual reception transducer consisting of M' adjacent reception transducers to which a delay sequence is applied.

Also optionally, a method for processing ultrasonic signals according to the invention may comprise an additional step for reconstructing a digital image of the area of interest from the denoised time signal array, particularly by means of synthetic total focusing processing.

It is also proposed a computer program downloadable from a communication network and/or saved on a computer-readable medium and/or executable by a processor, comprising instructions for executing steps of a method for processing ultrasonic signals according to the invention, when said program is executed on a computer.

It is also proposed an ultrasonic probing device comprising:
- a probe comprising a plurality of ultrasonic emission transducers and a plurality of ultrasonic reception transducers, and
- transducer control and processing means designed to implement a method for processing ultrasonic signals according to the invention.

Figure 2:
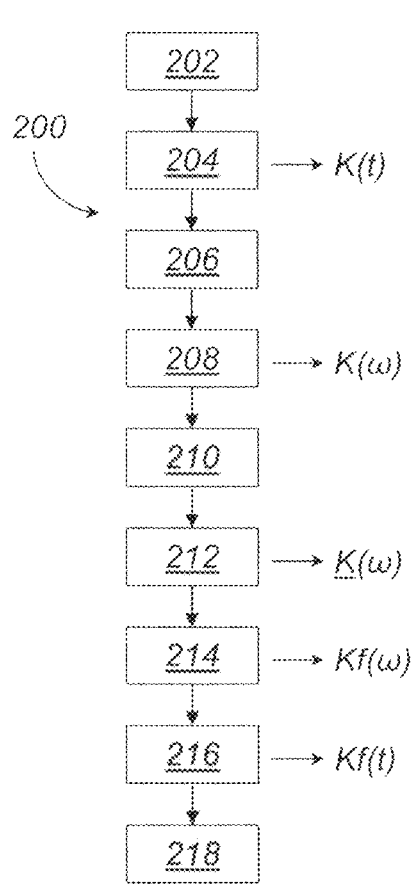
Figure 3:
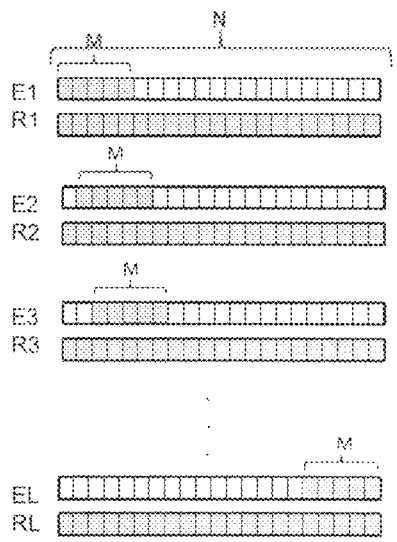
Figure 4:
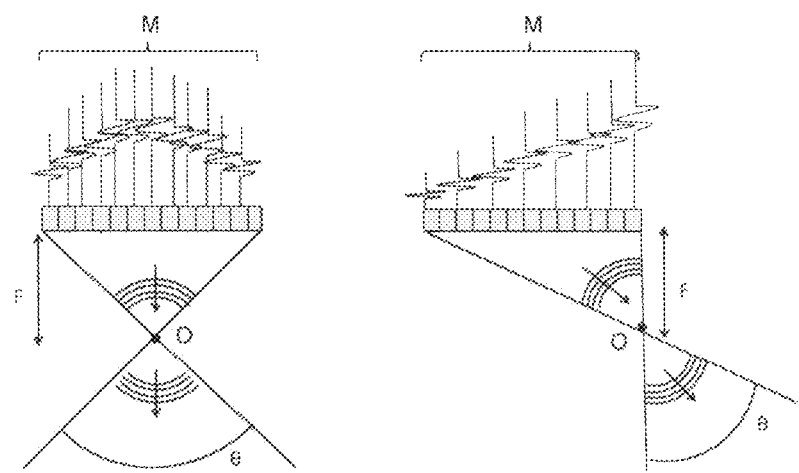
Figure 5:
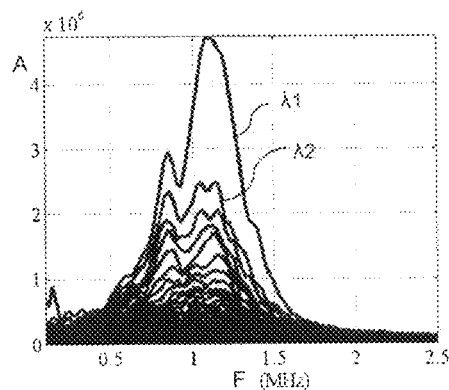
Figure 6:
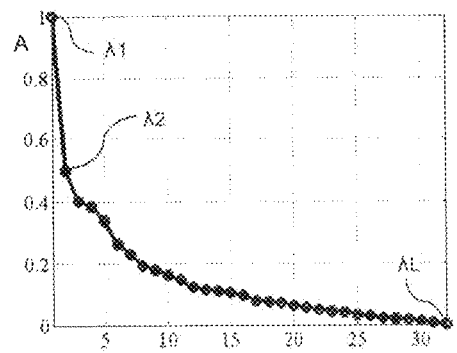
Figure 7:
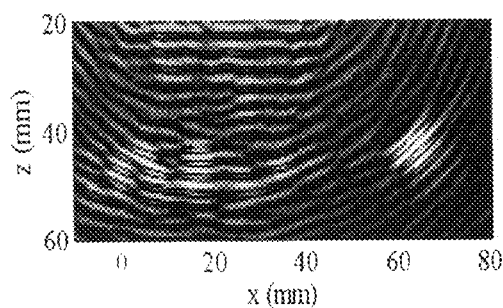
Figure 8:
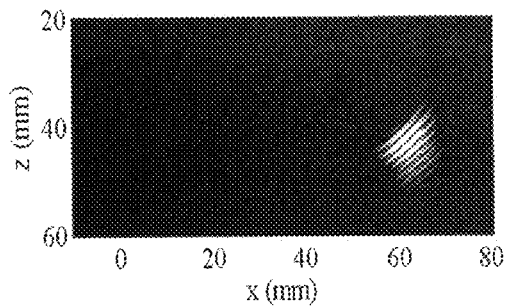

The invention will be understood more clearly using the description hereinafter, given merely by way of example and with reference to the appended drawings wherein:

FIG. 1 schematically represents the general structure of an ultrasonic probing device according to one embodiment of the invention, FIG. 2 illustrates the successive steps of a method for acquiring and processing ultrasonic signals implemented by the device in FIG. 1, according to one embodiment of the invention, FIGS. 3 and 4 illustrate an ultrasonic wave emission/reception principle implemented by the device in FIG. 1, FIGS. 5 and 6 illustrate, using diagrams, singular value distributions obtained from intermediate steps of the method in FIG. 2, FIGS. 7 and 8 comparatively illustrate ultrasound images obtained without and with full application of the method in FIG. 2.

With reference to FIG. 1, a device 100 for probing an object 102 according to one embodiment of the invention comprises an ultrasonic probe 104 having a housing 106, i.e. a non-deformable structural element acting as a reference attached to the probe 104, wherein, for example in a linear fashion or according to an array, N fixed or movable transducers $108_1, \ldots, 108_N$ are arranged.

The object 102 is for example a mechanical part to be examined by means of non-destructive testing or, in a medical context, a part of the human body to be monitored non-invasively. In the embodiment in FIG. 1, the object 102 is submerged in a liquid, such as water 110, and the probe 104 is kept at a distance from the object 102 so that water 110 separates the two. However in a further equivalent embodiment, the probe 104 could be in direct contact with the object 102.

The transducers $108_1, \ldots, 108_N$ are designed to emit ultrasonic waves toward the object 102 in response to control signals identified under the general reference C, along main directions parallel with each other, indicated by the dotted arrows in FIG. 1, and in a main plane which is that of the figure.

The transducers $108_1, \ldots, 108_N$ are further designed to detect echoes of ultrasonic waves reflected on or in the object 102 and to supply measurement signals identified under the general reference S and corresponding to these echoes. In this way, in the non-limiting example in FIG. 1, the transducers $108_1, \ldots, 108_N$ fulfill both an emission and reception function, but receivers different from the emitters could also be provided in different independent housings while remaining in compliance with the principles of the invention.

The probing device 100 further comprises an electronic circuit 112 for controlling the transducers $108_1, \ldots, 108_N$ of the probe 104 and for processing the measurement signals S. This electronic circuit 112 is connected to the probe 104 in order to transmit thereto the control signals C and in order to receive the measurement signals S. The electronic circuit 112 is for example that of a computer. It has a central processing unit 114, such as a microprocessor designed to emit to the probe 104 the control signals C and to receive from the probe 104 the measurement signals S, and a memory 116 wherein a computer program 118 is saved.

The computer program 118 firstly comprises instructions 120 for generating the control signals C for the transducers $108_1, \ldots, 108_N$ so as to:
- activate the transducers $108_1, \ldots, 108_N$ as emitters for L successive emissions of ultrasonic waves to an area of interest of the object 102,
- activate the transducers $108_1, \ldots, 108_N$ as receivers to, following each successive emission, simultaneously receive, via these N receivers and for a predetermined duration of the sought inspection depth, N measurement signals particularly measuring the noisy echoes due to reflections of each emission in the area of interest.

The set S of the L×N measurement signals transmitted by the transducers $108_1, \ldots, 108_N$ is returned by the probe 104 to the central processing unit 114.

The computer program 118 further comprises instructions 122 for constructing an array K(t) of ultrasonic time signals of the size L×N, each coefficient $K_{i,j}(t)$ of this array representing the measurement signal received by the transducer $108_j$ in response to the i-th emission.

Optionally, the computer program 118 further comprises instructions 124 for performing time filtering of the array K(t), this filtering being intended to delete any data situated at times of flight excluded from the area of interest in the object 102.

The computer program 118 further comprises instructions 126 for transforming the array K(t) into a frequency signal array K(ω) by means of a Fourier transform, advantageously by means of a discrete Fourier transform after time sampling of the coefficients of the array K(t), or, more advantageously, by means of FFT ("Fast Fourier Transform") computation if the number of samples of each coefficient of the array K(t) permits.

The computer program 118 further comprises instructions 128 for decomposing the frequency signal array K(ω) into singular values over a frequency band so as to diagonalize said array. This known operation makes it possible to estimate the arrays U, S and V such that:

$$K(\omega) = U.S.V^T$$
$$= \sum_{i=1}^{L} \lambda_i(\omega) \cdot u_i(\omega) \cdot v_i^T(\omega), \text{ where } U = [u_1(\omega), \ldots, u_L(\omega)]$$
$$\text{and } V = [v_1(\omega), \ldots, v_N(\omega)]$$

are orthogonal arrays of the respective sizes L×L and N×N, containing the singular vectors in reception and emission, i.e. the invariants in reception and emission of the time reversal operator, where S is a diagonal array of the size L×N containing the L singular values $\lambda_i(\omega)$ of the array $K(\omega)$, ordered in decreasing fashion at a given reference frequency $\lambda_1(\omega) \geq \ldots \geq \lambda_L(\omega) \geq 0$.

Optionally, the computer program 118 further comprises instructions 130 for reorganizing, according to the frequency, the array $K(\omega)$ into an array $\underline{K}(\omega)$ by reorganizing the frequency components of the singular values and singular vectors thereof. Indeed, if the echo of a defect is situated at a time of flight close to that of an interface of the object 102 (for example, a defect close to the base of the part), or if this echo has an amplitude similar to the structural noise, the same singular value of the array S may correspond equally to the defect, to the interface and to the structural noise according to the frequencies in question in the spectral bandwidth of the probe. This may advantageously merit a reorganization of the frequency components of the singular values and the corresponding frequency occurrences of the associated singular vectors, so as to optimize the correspondence between singular values and defects. The reorganized eigenvalues are annotated $\underline{\lambda}_1(\omega) \geq \ldots \geq \underline{\lambda}_L(\omega) \geq 0$.

The computer program 118 further comprises instructions 132 for reducing the rank of the array $\underline{K}(\omega)$ (or that of the array $K(\omega)$ if the optional instructions 130 are not executed), optionally reorganized, by removing some of the singular values $\underline{\lambda}_i$. This removal is performed according to a criterion for distinguishing between singular values associated with a defect and singular values associated with noise, the first having greater amplitudes than the second. Given that $\underline{\lambda}_1 \geq \ldots \geq \underline{\lambda}_L \geq 0$, it is necessary to find the value P between 1 and L such that $\underline{\lambda}_1, \ldots, \underline{\lambda}_P$ may be considered to be associated with defects to be detected in the object 102 and $\underline{\lambda}_{P+1}, \ldots, \underline{\lambda}_L$ may be removed as they are considered to be associated with noise. In practice, P is determined by studying the singular value amplitude decline curve and more specifically by studying the successive amplitude differences thereof (i.e. $\underline{\lambda}_2-\underline{\lambda}_1, \ldots, \underline{\lambda}_N-\underline{\lambda}_{N-1}$) at a reference frequency, for example the central frequency of the frequency spectrum of the array $\underline{K}(\omega)$. By way of non-limiting example, P may be equal to the index associated with the singular value for which the singular value decline curve exhibits a change of curvature, more specifically a change of slope, indicating a significant variation in the successive amplitude differences between singular values. Such a determination of P may be performed in a manner known per se by linear regression on the assumption of a two-stage linear decline. In the case of small defects ideally spaced out in respect of each other, P is equal to the number of defects present in the area of interest inspected. Reducing the rank of the array $\underline{K}(\omega)$ thus consists of only retaining Kf($\omega$) in the following equation:

$$\underline{K}(\omega) = Kf(\omega) + Kb(\omega), \text{ where:}$$

$$Kf(\omega) = \sum_{i=1}^{P} \underline{\lambda}_i(\omega) \cdot \underline{u}_i(\omega) \cdot \underline{v}_i^T(\omega) \text{ and } Kb(\omega) = \sum_{i=P+1}^{L} \underline{\lambda}_i(\omega) \cdot \underline{u}_i(\omega) \cdot \underline{v}_i^T(\omega).$$

The array Kf($\omega$) reconstructed in this way is a denoised frequency signal array, the noise subspace represented by the array Kb($\omega$) having been removed.

The computer program 118 further comprises instructions 134 for transforming the array Kf($\omega$) into a denoised time signal array Kf(t) by means of an inverse Fourier transform, advantageously by means of an inverse discrete Fourier transform, or, more advantageously, by IFFT ("Inverse Fast Fourier Transform") computation if the number of samples of each coefficient of the array Kf($\omega$) permits.

Finally, the computer program 118 comprises instructions 136 for performing synthetic total focusing as defined in the article mentioned above by C. Holmes et al on the denoised array Kf(t). A digital image of the area of interest is thus reconstructed wherein the quality is better than if the synthetic focusing had been carried out on the non-denoised array K(t). In particular, the SNR is enhanced.

With reference to FIG. 2, a method 200 for acquiring and processing ultrasonic signals implemented by the device 100 in FIG. 1 will now be described.

During a step 202, the processing unit 114 executing the instructions 120 controls the emission and reception sequences of the transducers $108_1, \ldots, 108_N$ for acquiring the array K(t).

These sequences are L in number, an integer between 1 and N−M+1, where M, an integer between 1 and N, is the number of adjacent transducers forming the emitting sub-aperture moving along the housing 106 of the probe 104 in intervals of at least one transducer. The choice of the number M is dependent on the quality sought of the spherical wave emitted by the sub-aperture. After each round, the signals are received on all of the N transducers, digitized and transmitted to the electronic circuit 112. FIG. 3 illustrates these emission and reception sequences, successively referenced E1 and R1, E2 and R2, E3 and R3, . . . , EL and RL, where the activated transducers are represented in gray tone.

In the case where M≥2, predetermined delay sequences are applied to the transducers forming the sub-aperture of M transducers. They enable focusing of the waves emitted at a point O situated at F mm in depth under the probe 104. The wavefront emitted does not stop at the point O. A wave diverges from this point and is propagated in the medium. For an observer situated at a depth greater than F, it is as if the divergent wave were from a virtual source located at 0. The virtual source created does not have a perfectly omni-directional directivity such as that of a point source but has an angular directivity having a relatively wide angle θ. This directivity may be adjusted by modifying the delays applied to the transducers of the sub-aperture such that the wave emitted by the virtual source is directed in a preferred direction in the object 102. This enhances the detection of the defects in this area. FIG. 4 illustrates the virtual source principle according to two delay sequences provided by way of example.

During a step 204, the processing unit 114 executing the instructions 122 constructs the array K(t), each coefficient $K_{i,j}(t)$ of this array representing the measurement signal received by the transducer $108_j$ in response to the i-th emission, this signal being digitized to facilitate the subsequent processing thereof.

During an optional step 206, the processing unit 114 executing the instructions 124 performs time filtering of the array K(t), this filtering being intended to delete any data situated at times of flight excluded from the area of interest. The aim of this step 206 is to subsequently facilitate the separation of the two subspaces represented by the arrays Kf($\omega$) and Kb($\omega$), in particular when the defects to be imaged are close to a significantly echoic interface, such as a base of a part. It makes it possible to limit the area to be imaged to a region close to the defects by particularly excluding the disturbing echoic interfaces. It is of particular interest in imaging cracks formed from the base of the object.

During a step 208, the processing unit 114 executing the instructions 126 performs a discrete Fourier transform of the array K(t) to obtain the frequency signal array K(ω).

During a step 210, the processing unit 114 executing the instructions 128 diagonalizes the array K(ω) by decomposing same into singular values, as above.

During an optional step 212, the processing unit 114 executing the instructions 130 reorganizes the array K(ω) into an array $\underline{K}(\omega)$ by reorganizing the frequency components of the singular values and singular vectors of the decomposition arrays S(ω), U(ω) and V(ω) into new decomposition arrays $\underline{S}(\omega)$, $\underline{U}(\omega)$ and $\underline{V}(\omega)$.

According to a first alternative embodiment for reorganizing the frequency components of the singular values and singular vectors, for each singular value $\lambda_i(\omega)$, $1 \le i \le L$:
- a reference frequency occurrence of a singular vector associated with $\lambda_i(\omega)$ is chosen, for example the singular vector of the array U, $u_i(\omega)$, this reference frequency occurrence being annotated $u_i^{ref} = u_i[\omega_{ref}]$ (this generally consists of the central frequency of the frequency spectrum of K(ω) for which a separation of the highest singular value is observed),
- the phase of this reference frequency occurrence $u_i^{ref}$ is computed, this phase is normalized in the interval [0,1], and then
- for each frequency ω of the frequency spectrum of K(ω):
  - the phases of the frequency occurrences $u_k[\omega]$ of the other singular vectors of the array U are computed and these phases are normalized in the interval [0,1],
  - the correlation between the normalized phase of $u_i^{ref}$ and the normalized phase of each $u_k[\omega]$ is computed,
  - the value j of k for which the correlation is greatest is determined, and
  - the value of $\lambda_j[\omega]$ is assigned to $\lambda_i[\omega]$, the value of $u_j[\omega]$ to $u_i[\omega]$, and the value of $v_j[\omega]$ to $v_i[\omega]$.

This gives new reorganized arrays $\underline{S}(\omega)$, $\underline{U}(\omega)$ and $\underline{V}(\omega)$ and thus a new reorganized array $\underline{K}(\omega) = \underline{U} \cdot \underline{S} \cdot \underline{V}^T$.

According to a second alternative embodiment for reorganizing the frequency components of the singular values and singular vectors, for each singular value $\lambda_i(\omega)$, $1 \le i \le L$:
- a reference frequency occurrence of a singular vector associated with $\lambda_i(\omega)$ is chosen, for example the singular vector of the array U, $u_i(\omega)$, this reference frequency occurrence being annotated $u_i^{ref} = u_i[\omega_{ref}]$ and corresponding to a maximum frequency occurrence of the singular value $\lambda_i(\omega)$ (this generally also consists of the central frequency of the frequency spectrum of K(ω)),
- the phase of this reference frequency occurrence $u_i^{ref}$ is computed, and then
- by defining a basic increment Δω for iteratively scanning the frequency spectrum of K(ω):
  - the phases of the frequency occurrences $u_k[\omega_{ref} \pm \Delta\omega]$ of the other singular vectors of the array U are computed, the correlation between the phase of $u_i^{ref}$ and the phase of each $u_k[\omega_{ref} \pm \Delta\omega]$ is computed, the value j of k for which the correlation is greatest is determined, and the value of $\lambda_j[\omega_{ref} \pm \Delta\omega]$ is assigned to $\lambda_i[\omega_{ref} \pm \Delta\omega]$, the value of $u_j[\omega_{ref} \pm \Delta\omega]$ to $u_i[\omega_{ref} \pm \Delta\omega]$, and the value of $v_j[\omega_{ref} \pm \Delta\omega]$ to $v_i[\omega_{ref} \pm \Delta\omega]$,
  - as the new reference frequency occurrence, that of the singular vector having maximized the correlation with the previous step at the frequency $\omega_{ref} \pm \Delta\omega$ is adopted and the correlation computations of the previous step at $\omega_{ref} + 2\Delta\omega$ are repeated,
  - the study of K(ω) in the spectral bandwidth of the probe is thus continued step by step until the limits thereof.

New reorganized arrays $\underline{S}(\omega)$, $\underline{U}(\omega)$ and $\underline{V}(\omega)$ and therefore a new reorganized array $\underline{K}(\omega) = \underline{U} \cdot \underline{S} \cdot \underline{V}^T$ are thus obtained.

The reorganized array $\underline{K}(\omega)$ is thus now decomposed into singular values each having singular vectors optimizing the correlations thereof at all frequencies, either in relation to a selected constant reference frequency (first alternative embodiment), or step by step (second alternative embodiment). In this way, after reorganizing the array $\underline{K}(\omega)$, a defect is associated with the same singular value for all the frequencies in the spectral band of the probe. An example of frequency distributions in respect of amplitude (A) of L eigenvalues is illustrated in FIG. 5. The normalized amplitude decline of these eigenvalues, either on average in the frequency spectrum of the array $\underline{K}(\omega)$, or at a selected central frequency, is for example illustrated in FIG. 6: in this example, a significant difference in amplitude is observed between the first and second singular values.

During a step 214, the processing unit 114 executing the instructions 132 reduces the rank of the array $\underline{K}(\omega)$ (or that of the array K(ω) if the previous optional step was not executed) only retaining $$Kf(\omega) = \sum_{i=1}^{P} \underline{\lambda}_i(\omega) \cdot \underline{u}_i(\omega) \cdot \underline{v}_i^T(\omega).$$

During a step 216, the processing unit 114 executing the instructions 134 performs a discrete inverse Fourier transform of the array Kf(ω) to obtain the denoised time signal array Kf(t).

Finally, during a final step 218, the processing unit 114 executing the instructions 136 reconstructs a digital image of the effective area of interest by synthetic focusing on the basis of the denoised array Kf(t). By way of comparison, FIGS. 7 and 8 illustrate examples of reconstructed digital images, either directly after the step 204 for constructing the array K(t) for FIG. 7, or after executing all the steps 202 to 216 for FIG. 8.

It should be noted that, in concrete terms, the examples illustrated in FIGS. 5 to 8 were obtained by experimenting on a noisy part made of austenoferritic steel, 70 mm in thickness wherein an artificial 2 mm diameter Generatrix Hole (GH) is machined, at a depth of 40 mm. It sought to image the defect using a 1.1 MHz central frequency sensor consisting of 64 emitting/receiving transducers. Given the inter-element interval (i.e. the width of a transducer in addition to the space between two adjacent transducers) of the sensor (1.4 mm) and the depth of the defect, only the 32 central elements are activated. By way of an example of application, this sensor is placed on the object 102 45° from the GH defect. To enhance the acquisition in relation to a conventional FMC acquisition, the emissions were performed using a sub-aperture consisting of M=7 transducers (38 central elements are then activated for 32 successive emissions) and the delay sequence applied was defined for 7 transducers and such that the waves emitted are essentially oriented at 45°.

It appears clearly that a method and a device such as those detailed above are suitable for effectively denoising the ultrasonic signals acquired in the form of an array K(t) as defined above.

It should further be noted that the invention is not limited to the embodiment described above. It would be obvious to those skilled in the art that various modifications may be made to the embodiment described above, in the light of the teaching disclosed herein.

In particular, the computer program instructions could be replaced by electronic circuits dedicated to the functions carried out during the execution of these instructions.

As a general rule, in the claims hereinafter, the terms used should not be interpreted as limiting the claims to the embodiment disclosed in the present description, but should be interpreted to include any equivalents intended to be covered by the claims due to the wording thereof and which can be envisaged by those skilled in the art by applying their general knowledge to the implementation of the teaching disclosed herein.

The invention claimed is:

1. A method for processing ultrasonic signals acquired by ultrasonic probing, comprising:
controlling a plurality of emission transducers for L successive emissions of ultrasound waves to an area of interest;
controlling N reception transducers to simultaneously receive and for a predetermined time, for each successive emission, N measurement signals, and measuring noisy echoes due to reflections of the emission in question in the area of interest;
obtaining an array of ultrasonic time signals of size L×N, each coefficient $K_{i,j}(t)$ of the array representing the measurement signal received by the j-th reception transducer due to the i-th emission;
transforming the time signal array into a frequency signal array;
performing a singular value decomposition of the frequency signal array;
denoising the ultrasonic time signal array by:
removing some of singular values and associated singular vectors obtained from the singular value decomposition according to a predetermined criterion for distinguishing between singular values associated with defects and singular values associated with noise, the criterion being based on difference values, wherein each difference value is computed as a difference between successive amplitudes of singular values in a decreasing series of amplitudes of the singular values determined on the basis of the frequency signal array;
reconstructing a denoised frequency signal array on the basis of unremoved singular values and singular vectors, and
performing an inverse transform of the denoised frequency signal array into a denoised time signal array.

2. The method for processing ultrasonic signals according to claim 1, wherein the predetermined criterion for distinguishing between singular values associated with defects and singular values associated with noise is a curvature change criterion in the decreasing series of singular value amplitudes.

3. The method for processing ultrasonic signals according to claim 1, wherein the predetermined criterion for distinguishing between singular values associated with defects and singular values associated with noise is a change of slope criterion in the decreasing series of singular value amplitudes.

4. The method for processing ultrasonic signals according to claim 1, wherein the transform and inverse transform are discrete Fourier transforms.

5. The method for processing ultrasonic signals according to claim 1, further comprising, before the denoising, filtering the time signal array by deleting any data situated at times of flight excluded from the area of interest.

6. The method for processing ultrasonic signals according to claim 1, further comprising reorganizing frequency components of the singular values and singular vectors of the frequency signal array on the basis of an optimization of correlations between frequency occurrences of the singular vectors to optimize a correspondence between singular values and defects in the area of interest and thus optimize noise filtering.

7. The method for processing ultrasonic signals according to claim 1, wherein, at each successive emission, M adjacent emission transducers are activated and a delay sequence is applied to the M emission transducers to emit a spherical wave from a virtual source situated at a predetermined distance from the plurality of emission transducers.

8. The method for processing ultrasonic signals according to claim 1, wherein each reception is performed by virtual reception transducers, each virtual reception transducer of adjacent reception transducers to which a delay sequence is applied.

9. The method for processing ultrasonic signals according to claim 1, further comprising reconstructing a digital image of the area of interest from the denoised time signal array, by synthetic total focusing processing.

10. A non-transitory computer readable medium including a computer program executable by a processor, comprising instructions for executing a method for processing ultrasonic signals according to claim 1, when the program is executed on a computer.

11. An ultrasonic probing device comprising:
a probe comprising a plurality of ultrasonic emission transducers and a plurality of ultrasonic reception transducers, and
transducer control and processing means configured to implement a method for processing ultrasonic signals according to claim 1.

* * * * *